US009821138B2

(12) United States Patent
Plata

(10) Patent No.: US 9,821,138 B2
(45) Date of Patent: *Nov. 21, 2017

(54) INTRACAVITY BALLOON CATHETER

(71) Applicant: Myriad Medical LLC, Tampa, FL (US)

(72) Inventor: Fernando Plata, Atlanta, GA (US)

(73) Assignee: MYRIAD MEDICAL, LLC, Tampa, FL (US)

( * ) Notice: Subject to any disclaimer, the term of this patent is extended or adjusted under 35 U.S.C. 154(b) by 118 days.

This patent is subject to a terminal disclaimer.

(21) Appl. No.: 14/464,121

(22) Filed: Aug. 20, 2014

(65) Prior Publication Data

US 2014/0357942 A1 Dec. 4, 2014

Related U.S. Application Data

(63) Continuation of application No. 13/157,510, filed on Jun. 10, 2011, now Pat. No. 8,840,542.

(60) Provisional application No. 61/353,338, filed on Jun. 10, 2010.

(51) Int. Cl.

*A61M 25/10* (2013.01)
*A61M 25/00* (2006.01)
*A61N 5/10* (2006.01)

(52) U.S. Cl.

CPC ........... *A61M 25/0012* (2013.01); *A61N 5/10* (2013.01); *A61M 2025/0008* (2013.01); *A61M 2025/1059* (2013.01); *A61M 2025/1086* (2013.01); *A61N 2005/1097* (2013.01)

(58) Field of Classification Search

CPC .................. A61M 25/1002; A61M 2025/1059
See application file for complete search history.

(56) References Cited

U.S. PATENT DOCUMENTS

| | | | |
|---|---|---|---|
| 5,355,087 | A | 10/1994 | Claiborne et al. |
| 5,479,095 | A | 12/1995 | Michalek et al. |
| 8,080,031 | B2 | 12/2011 | Isham |
| 8,241,317 | B2 | 8/2012 | Isham et al. |
| 8,454,648 | B1 | 6/2013 | Isham |
| 8,500,618 | B2 | 8/2013 | Isham |
| 8,500,771 | B2 | 8/2013 | Isham |
| 8,603,129 | B2 | 12/2013 | Isham |
| 8,679,147 | B2 | 3/2014 | Isham |
| 8,840,542 | B2 | 9/2014 | Plata |

(Continued)

FOREIGN PATENT DOCUMENTS

| | | |
|---|---|---|
| EP | 0 720 836 A2 | 7/1996 |
| EP | 0 720 836 A3 | 7/1996 |

(Continued)

OTHER PUBLICATIONS

International Search Report dated Sep. 16, 2011 for PCT/US2011/039957 filed Jun. 10, 2011.

(Continued)

*Primary Examiner* — John Lacyk
*Assistant Examiner* — Thaddeus Cox
(74) *Attorney, Agent, or Firm* — Brinks Gilson & Lione

(57) ABSTRACT

A device and method for minimizing exposure of soft mucosa tissues to radiation, the device including a low-volume intracavity balloon catheter having multiple expansion portions, including an isometrically expanding portion and a substantially planar anterior portion.

12 Claims, 3 Drawing Sheets

10
18
30
32
14
16
40
44
19
12
24
13
28
22
26
20

(56) References Cited

U.S. PATENT DOCUMENTS

| | | | | |
|---|---|---|---|---|
| 9,126,035 | B2 | 9/2015 | Valoir | |
| 9,227,084 | B2 | 1/2016 | Isham et al. | |
| 9,381,334 | B2 | 7/2016 | Isham | |
| 2002/0010489 | A1* | 1/2002 | Grayzel | A61F 2/958 606/194 |
| 2003/0028097 | A1 | 2/2003 | D'Amico et al. | |
| 2007/0010845 | A1* | 1/2007 | Gong | A61B 17/8855 606/192 |
| 2008/0021385 | A1* | 1/2008 | Barry | A61L 27/34 604/103.02 |
| 2008/0300619 | A1 | 12/2008 | Isham | |
| 2009/0221899 | A1 | 9/2009 | Isham | |
| 2009/0276031 | A1 | 11/2009 | Kao | |
| 2010/0145379 | A1* | 6/2010 | Isham | A61B 5/411 606/192 |
| 2011/0044566 | A1 | 2/2011 | Fish et al. | |
| 2012/0078177 | A1 | 3/2012 | Isham | |
| 2014/0051968 | A1 | 2/2014 | Isham et al. | |

FOREIGN PATENT DOCUMENTS

| | | | |
|---|---|---|---|
| EP | 1 060 757 | A1 | 12/2000 |
| WO | WO 97/21462 | | 6/1997 |
| WO | WO 00/21584 | | 4/2000 |
| WO | WO 02/07795 | | 1/2002 |
| WO | WO 2007/065137 | | 6/2007 |
| WO | WO 2007/098416 | | 8/2007 |
| WO | WO 2009/152470 | | 12/2009 |
| WO | WO 2012/118919 | A1 | 9/2012 |
| WO | WO 2013/066566 | A1 | 5/2013 |

OTHER PUBLICATIONS

Extended European Search Report, EP App. No. 16150382.6, published Jul. 13, 2016, report dated May 31, 2016, 7 pages.

* cited by examiner

INTRACAVITY BALLOON CATHETER

CROSS REFERENCE TO RELATED APPLICATIONS

The present application is a continuation of U.S. application Ser. No. 13/157,510, filed Jun. 10, 2011, now U.S. Pat. No. 8,840,542, which claims the benefit under 35 U.S.C. §119(e) to U.S. Provisional Application No. 61/353,338, filed Jun. 10, 2010, the disclosures of which are hereby incorporated herein by reference in their entirety.

FIELD OF THE INVENTION

This invention relates generally to the field of diagnostic and therapeutic treatment of disease. In particular, the present invention relates to an intracavity balloon catheter and method of use thereof to protect and stabilize the prostate region during staging process and radiation therapy treatment.

BACKGROUND OF THE INVENTION

Radiation therapy treatment of soft tissue tumors in the prostate using radiation therapy treatment is complicated by the proximity of the prostate to radiation-sensitive tissues. Radiation therapy treatment of the prostate is further complicated by prostate motion.

Typically, the planning of radiation therapy for the treatment of prostate cancer involves the patient undergoing a CT-based simulation scan of the pelvis to determine the location of the prostate gland. In the simulation procedure, the patient is placed on CT and/or MRI equipment that is similar to the radiation treatment equipment, except that it does not generate the high energy radiation beam. The simulation equipment is positioned to simulate the conditions experienced by the patient during delivery of the sequence of treatment beams prescribed by the treating oncologist. Normally, during the simulation procedure, CT and/or MRI images are acquired. These CT and/or MRI images allow the oncologist to locate the position of the tumor and develop a radiation treatment plan using a devoted radiation or proton therapy treatment plan. This treatment plan delineates the positions of the radiation equipment components for precise delivery of the radiation to a predetermined area.

During the subsequent treatment procedure, the patient is placed in the same position on the treatment equipment as in the simulation scans. Radiation-emitting devices are generally known and used for radiation therapy in the treatment of patients. During treatment, a radiation beam is delivered to the patient at the precise location as delineated by the physician during simulation. A further feature of radiation therapy involves portal images, which are commonly used to verify and record tumor location.

During external beam radiation, radiation is directed to the prostate, which is near the rectal wall. Rectal bleeding following radiotherapy is common, on the order of 20-30%, which translates into at least 10,000 men a year following treatment of prostate cancer. The cause of rectal bleeding following radiotherapy is overdosage of the rectum with radiation. The high incidence of rectal bleeding limits the total dose of radiation one can give the prostate cancer and therefore limits the potential cure rate for radiotherapy.

A large amount of attention has been directed to reducing the amount of rectal bleeding resulting from radiotherapy. One of the main ways physicians limit rectal bleeding is that they decrease the total radiation dose used to treat the patient's prostate cancer. However, this may lead to inadequate radiation treatment and a higher probability of local cancer recurrence. Another method physicians have used in an attempt to reduce rectal bleeding following radiotherapy is to use a daily balloon rectal catheter to immobilize the prostate. The most common and oldest balloon catheter methods use a balloon that inflates in the rectum behind the prostate. The mechanism of action is to force the posterior rectum away from the prostate. This mechanism of action is of very limited efficacy because the posterior rectum is rarely a cause of rectal bleeding. Of most concern for rectal bleeding is the anterior rectum that is directly adjacent to the posterior prostate.

More recent attempts at minimizing rectal bleeding using balloon catheters have been aimed at forcing the prostate into a fixed position to allow the radiation beam to be more precisely directed to the target tissue. The balloon catheter apparatuses disclosed in the prior art attempt to stabilize the prostate by using large-volume balloons (e.g. 100 cc or more) and, in some cases, have various protrusions that attempt to create a seating area to receive and immobilize the prostatic bulge. Large volume balloons and balloons with bulges distort the rectal mucosa to seat or "cup" the prostate. Large volume balloons also increase patient discomfort.

U.S. Pat. No. 5,476,095 and U.S. Patent Publication No. 2003/028097 both disclose a rectal balloon apparatus having an inner balloon and an outer balloon, and an overall balloon shape that is round with a saddle-shaped bulge on the anterior surface of the balloon. The inner balloon has an anterior section that is covered with an inelastic, adhesive backed cloth material. As the device is inflated, the inner balloon forces the anterior surface of the outer balloon against the prostatic region of the rectum. More specifically, as the balloon is inflated to approximately 60 cc, a saddle-shaped bulge receives the rectal prostatic bulge inferior to the ampulla of the rectum.

U.S. Patent Publication No. 2009/0221899 discloses a rectal balloon apparatus wherein the balloon element has two inflated conditions. The first inflated condition, occurring when approximately 100 cc of fluid are introduced into the balloon, creates a flat surface with a seating area for the prostate to rest. In the second inflated position, a bulbous portion protrudes from the balloon at a position adjacent to the tip of the balloon. This protrusion occurs when at least 140 cc of fluid are introduced into the balloon. The purpose of the bulbous portion is to better isolate the prostate.

The methods and balloon catheter apparatuses in the prior art have not adequately addressed the problem of rectal bleeding, as between 20-30% of men still experience rectal bleeding during radiation therapy treatments. Moreover, the use of large volume balloons and balloons with bulges that protrude into the anterior rectum to receive the prostatic bulge increase patient discomfort.

SUMMARY OF THE INVENTION

The present invention in one of its ideal embodiments relates to an intracavity catheter, and more specifically an intrarectal balloon catheter and method of using the catheter for immobilizing the prostate during staging and related radiation therapy treatment. The foregoing problems associated with the use of high-volume balloons or balloons with bulges, namely rectal bleeding and pain, have been significantly reduced by the use of an intracavity balloon catheter according to the present invention.

It has been learned that the size in cubic centimeters of the high radiation dose region directly adjacent to the prostate is an important factor in determining the incidence and severity of rectal bleeding caused by radiation injury using modern treatment techniques. The intracavity balloon catheter according to the present invention reduces the amount of anterior rectal mucosa exposed to high radiation doses by having a small volume balloon made of a thin, elastic, and durable material with a modified anterior rectal interface that spares rectal tissue while still effectively immobilizing the prostate gland. The disclosed anterior rectal interface minimizes expansion in the anterior direction, and can be modified to allow outpouching of the anterior rectal mucosa. By not compressing the tissues of the anterior rectum into a smooth, flat layer against the posterior prostate, the volume of continuous anterior rectal mucosa adjacent to the posterior prostate that could receive an excessive does of radiation is reduced. The use of a smaller volume balloon of thinner and more flexible material will also alleviate some patient discomfort during the simulation and treatment phases.

The intracavity balloon catheter of the present invention includes a small-diameter, flexible catheter having a proximal catheter portion, a distal catheter portion, and a fluid passageway there between. The intracavity balloon catheter includes a balloon disposed at the distal end of the catheter, with the balloon having an exterior surface moveable between a deflated condition and an inflated condition by introduction of up to 80 cc of fluid from the catheter into the lumen. The tip of the distal portion of the catheter extends into the balloon lumen. In an alternative embodiment, the distal portion of the catheter can be connected to the anterior surface of the lumen of the balloon to restrict rotation between the catheter and the balloon. Exemplary mechanisms of connecting the distal portion of the catheter to the interior anterior surface of the balloon include through mechanical connection, chemical bonding or welding process.

The exterior surface of the balloon includes a reinforced anterior surface. In the inflated condition, the reinforced anterior surface remains substantially planar, exhibiting only a minimal degree of curvature in the anterior direction. The majority of the exterior surface of the balloon has a higher elasticity than the reinforced anterior surface and expands isometrically away from the reinforced anterior surface.

In the deflated position, the balloon creates a catenary shape facilitated by the reinforced portion of the balloon. The catenary shape allows the balloon to be folded around the catheter which facilitates entry of the catheter and balloon device into the cavity of the patient. The balloon may be covered with radioprotective elements such as Vitamin A, Vitamin E, misoprostal, amifostine, formalin solution and sulfasalazine to provide additional protection to the rectal mucosa. The radioprotective elements may be chemically bonded to the balloon during the manufacturing process, or may be applied to the balloon prior to insertion. The catheter of the intracavity balloon catheter includes a positioning ring longitudinally adjustable between the balloon and the proximal portion of the catheter to secure the catheter and prevent longitudinal movement after insertion into the cavity of the patient and to assist in recreating exact balloon position on different treatment days.

The reinforced anterior surface of the balloon can include a support surface to provide support to the posterior prostate. The support surface can include a plurality of support elements such as longitudinal ridges, obround knobs or hemispherically-shaped elements elevated relative to the support surface. The support elements can be spaced apart to allow the anterior rectal mucosa to outpouch between the elements, thereby reducing the amount of pressure on and compression of the anterior rectal mucosa at the anterior surface of the balloon. The outpouching thus prevents the anterior rectal mucosa from forming a smooth, flat layer against the posterior prostate thereby reducing the contiguous volume of anterior rectal mucosa exposed to high levels of radiation during radiation treatment.

Prior to use of the intracavity balloon catheter, the patient can be prepared for insertion of the device into the rectum. The intracavity balloon catheter is removed from the packaging, folded around the catheter and lubricant added to reduce the trauma of insertion. The catheter is inserted to a pre-determined depth and in a manner so the reinforced anterior surface of the balloon is adjacent to the posterior prostate. The balloon is then inflated using an inflating device connected to the catheter until a volume of up to 80 cc is achieved. The intracavity balloon catheter can then be secured against the external sphincter of the patient to prevent longitudinal movement by using a positioning ring longitudinally adjustable between the balloon and the proximal portion of the catheter.

BRIEF DESCRIPTION OF THE DRAWINGS

Similarly.

Similarly.

DETAILED DESCRIPTION OF THE DRAWINGS

The following detailed description and the appended drawings describe and illustrate exemplary embodiments of the invention solely for the purpose of enabling one of ordinary skill in the relevant art to make and use the invention. As such, the detailed description and illustration of these embodiments are purely exemplary in nature and are in no way intended to limit the scope of the invention, or its protection, in any manner. It should also be understood that the drawings are not to scale and in certain instances details have been omitted, which are not necessary for an understanding of the present invention, such as conventional details of fabrication and assembly.

Figure 1:
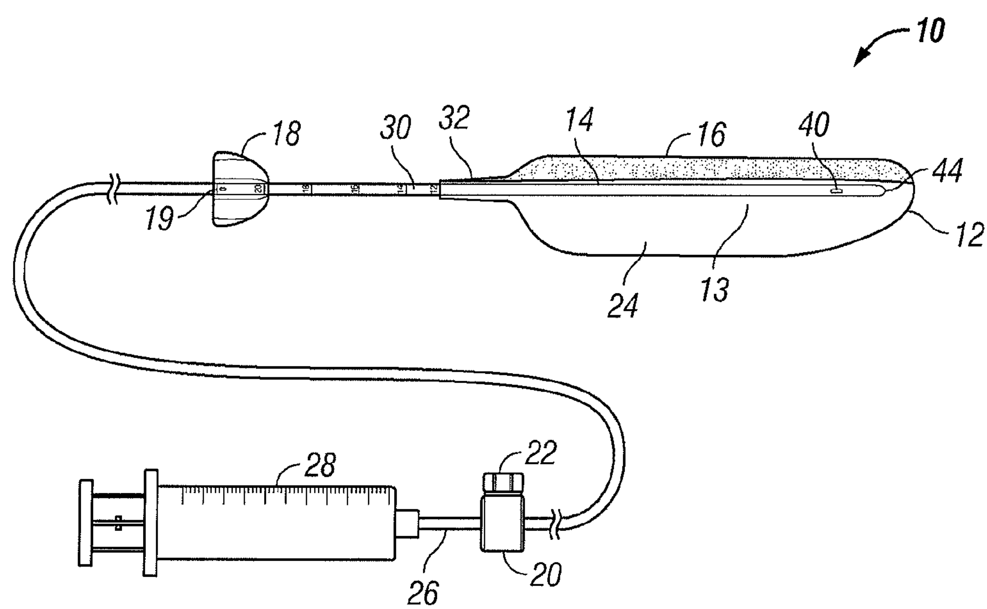
FIG. 1 is a side elevational view of the intracavity balloon catheter of the present invention in an inflated condition.

Referring first to FIG. 1, one embodiment of the present invention includes an intracavity balloon catheter 10 with a flexible catheter 14 having a distal end 13, a proximal end 15, and a fluid passageway there between. The catheter 14 has a balloon 12 disposed at the distal end 13 and welded to the catheter 14 at weld area 32. The distal tip of the catheter 44 extends into the lumen of the balloon 12 and has a hole 40 which allows fluid to pass into the lumen and move the balloon 12 from its deflated condition to its inflated condition.

The balloon 12 is made of a thin, elastic material such as PVC, polyurethane or a similar material. The balloon has an anterior surface 16 and a bottom portion 24. The anterior surface 16 is reinforced with silicone or another semi-flexible material. The reinforced nature of the anterior surface 16 gives it less elasticity than the bottom portion 24. When the balloon 12 inflates, the reinforced anterior surface 16 remains substantially planar with minimal curvature in the anterior direction. During inflation, the bottom portion 24 expands isometrically and primarily in the posterior direction to provide intracavity stability without forcing the reinforced anterior surface 16 into the anterior tissue of the cavity, thereby reducing the pressure on and compression of the anterior tissue.

Figure 3:
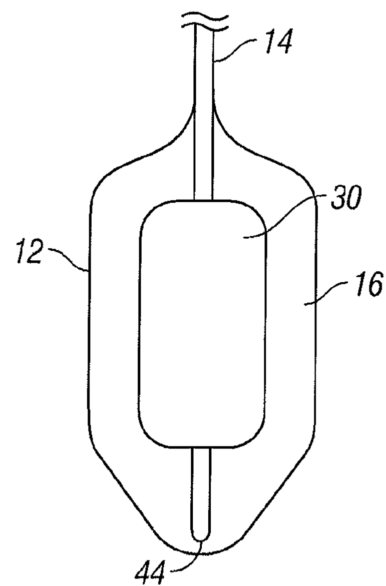
FIG. 3 shows a top view of the intracavity balloon catheter in the inflated condition with the anterior reinforced surface having a support area.
Figure 4:
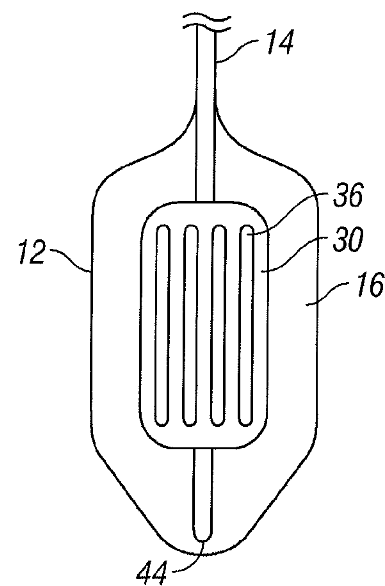
FIG. 4 shows a top view of the intracavity balloon catheter in the inflated condition with the anterior reinforced surface having a support area having a plurality of longitudinal ridges elevated relative to the support area.
Figure 5:
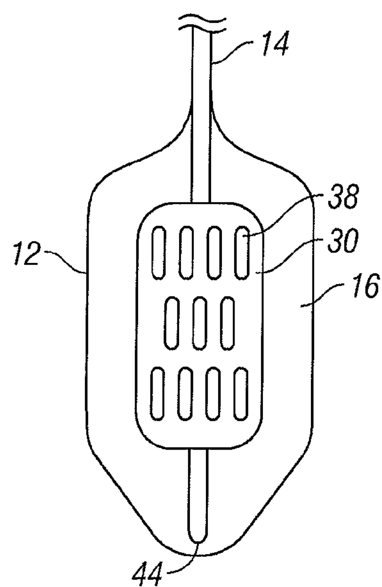
FIG. 5 shows a top view of the intracavity balloon catheter in the inflated condition with the anterior reinforced surface having a support area having a plurality of obround knobs elevated relative to the support area.
Figure 6:
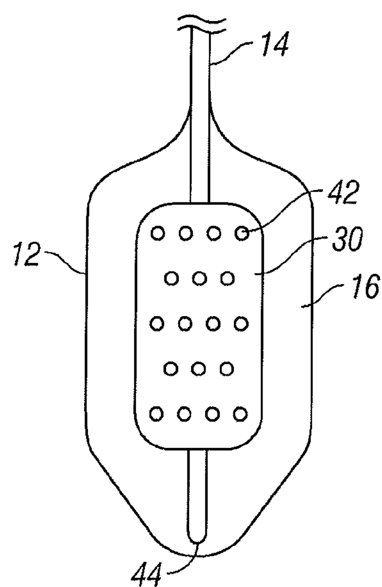
FIG. 6 shows a top view of the intracavity balloon catheter in the inflated condition with the anterior surface having a support area having a plurality of hemispherically-shaped elements elevated relative to the support area.

FIG. 3 shows a top view of the balloon 12 in its inflated condition with the reinforced anterior surface 16 having a support area 30. FIG. 4 shows a top view of the balloon 12 with the support area 30 having a plurality of longitudinal ridges 36 elevated relative to the support area 30. Similarly, FIG. 5 shows a top view of the balloon 12 with the support area 30 having a plurality of obround-shaped knobs 38 elevated relative to the support area 30. FIG. 6 shows yet another embodiment of the support area 30 having a plurality of hemispherically-shaped support elements 42 elevated relative to the support area 30.

As shown in FIG. 1, the catheter 14 has a valve assembly 20 affixed to it opposite the balloon 12. The valve cock 22 of the assembly 20 allows fluids to selectively pass through the shaft 14 into the balloon 12 using an inflating device, such as a syringe 28, connected to the port 26 of the catheter 14. The catheter 14 has numerical markings 30 which indicate the distance that the balloon 12 has been inserted into the cavity. The catheter 14 includes a positioning ring 18 made of semi-rigid material that is longitudinally adjustable between the balloon 12 and the proximal end of the catheter 15 and can be secured with a latch 19.

Figure 2:
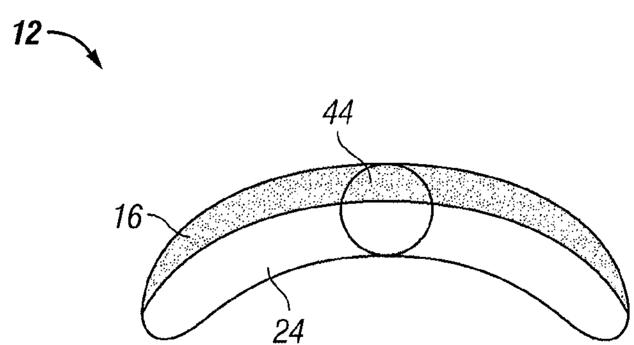
FIG. 2 shows the front view of the balloon in a deflated position partially collapsed around the catheter of the balloon.

FIG. 2 shows a front view of the distal end of the intracavity balloon catheter 10 in which the balloon 12 is in the deflated condition. The reinforced anterior surface 16 causes the balloon 12 in its deflated state to form a catenary shape and partially collapse around catheter 14. The reinforced anterior surface 16 collapses around the tip of the catheter 44 which prevents the tip 44 from protruding from the balloon 12 during the insertion of the balloon catheter 10 into the cavity.

Figure 7:
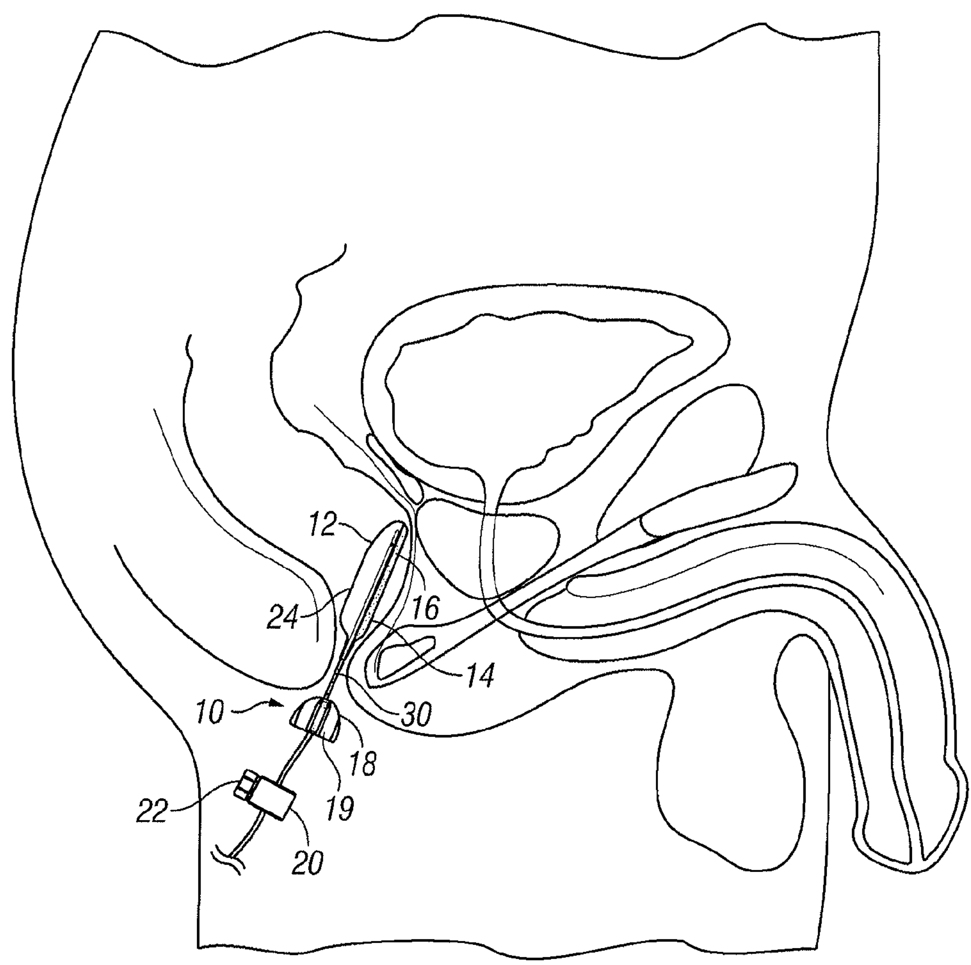
FIG. 7 shows the method of using the intracavity balloon catheter, in the inflated condition, for immobilizing the prostate during staging process and radiation therapy treatment.

FIG. 7 shows a method of using the intracavity balloon catheter 10. FIG. 7 shows the intracavity balloon catheter 10 in the anal cavity with the balloon 12 in the inflated position. The desired depth is attained through use of the numerical markings 30 on the catheter 14. The external positioning ring 18 is placed against the external sphincter and secured with the latch 19 to prevent migration of the device 10 superiorly during use. The planar anterior surface 16 rests against the anterior rectal mucosa and the more elastic bottom portion 24 of the balloon 12 is expanded isometrically.

The balloon can be coated with radioprotective materials to provide further protection to the rectal mucosa against the negative effects of radiation therapy. Exemplary radioprotective elements include Vitamin A, Vitamin E, misoprostal, amifostine, formalin solution and sulfasalazine. The radioprotective material can be chemically bonded to the balloon during the manufacturing process or it can be applied to the balloon prior to insertion.

Alternatively, the balloon can have both a reinforced anterior surface and reinforced posterior surface with less elasticity than the lateral surfaces of the balloon. During inflation, expansion would occur in the lateral directions and both the reinforced anterior surface and the reinforced posterior surface would remain substantially planar, thereby reducing compression of the rectal mucosa in both the anterior and posterior directions. The distal portion of the catheter can be connected to the anterior surface of the lumen of the balloon to restrict rotation between the catheter and the balloon. Exemplary mechanisms of connecting the distal portion of the catheter to the interior anterior surface of the balloon include through mechanical connection, chemical bonding or welding process.

What is claimed is:

1. An intracavity balloon catheter, comprising:

a flexible catheter having a proximal catheter portion, a distal catheter portion having a distal tip, and a fluid passageway between the distal tip and the proximal catheter portion; and a balloon disposed at the distal tip of the catheter, the balloon comprising a balloon lumen, an exterior balloon surface having a posterior portion and a reinforced anterior portion, said exterior balloon surface moveable between a deflated condition and an inflated condition by introduction of up to 80 cc of fluid into the lumen, and an isometrically expanding posterior balloon portion having a higher elasticity than the reinforced anterior balloon portion, the posterior balloon portion comprising a majority of the exterior balloon surface, wherein the balloon has an outer diameter expandable in the inflated condition; and wherein the reinforced anterior portion surface exhibits only a minimum degree of curvature in an anterior direction in a fully inflated position of the balloon.

2. The intracavity balloon catheter according to claim 1, wherein the balloon in its deflated condition forms a catenary insertion portion along a distal end of the catheter.

3. The intracavity balloon catheter according to claim 2, wherein the catheter further comprises a positioning ring longitudinally adjustable between the balloon and the proximal portion of the catheter.

4. The intracavity balloon catheter according to claim 3, further comprising a support surface provided on an area of the exterior balloon surface, the support surface substantially planar in the inflated condition.

5. The intracavity balloon catheter according to claim 4, wherein the support surface comprises a plurality of longitudinal ridges elevated relative to the support surface.

6. The intracavity balloon catheter according to claim 4, wherein the support surface comprises a plurality of obround knobs or supports elevated relative to the support surface.

7. The intracavity balloon catheter according to claim 4, wherein the support surface comprises a plurality of hem ispherically-shaped supports elevated relative to the support surface.

8. The intracavity balloon catheter according to claim 2, further comprising radioprotective material selected from the group consisting of Vitamin E, Vitamin A, misoprostal, amifostine, formalin solution, and sulfasalazine chemically bonded to the balloon during the manufacturing process.

9. The intracavity balloon catheter according to claim 1, further comprising a reinforced posterior portion forming a substantially planar surface in the inflated condition.

10. The intracavity balloon catheter according to claim 1, wherein the distal portion of the catheter is connected to an anterior surface of the balloon.

11. The intracavity balloon catheter according to claim 1, wherein the lumen is expandable in the inflated condition between a substantially circular cross section and a substantially non-circular cross section.

12. The intracavity balloon catheter according to claim 1, further comprising a plurality of hem ispherically-shaped supports provided on a surface of the anterior balloon portion.

* * * * *